(12) United States Patent
Olsen

(10) Patent No.: US 7,766,885 B2
(45) Date of Patent: Aug. 3, 2010

(54) DRUG DELIVERY SYSTEM

(75) Inventor: James M. Olsen, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 1822 days.

(21) Appl. No.: 10/862,775

(22) Filed: Jun. 7, 2004

(65) Prior Publication Data
US 2005/0273082 A1   Dec. 8, 2005

(51) Int. Cl.
*A61M 11/00*   (2006.01)

(52) U.S. Cl. ............. 604/288.04; 604/141; 604/288.01; 604/288.03

(58) Field of Classification Search .......... 604/9, 604/118, 141, 144, 146, 288.01, 288.04, 604/93.01, 891.1
See application file for complete search history.

(56) References Cited

U.S. PATENT DOCUMENTS

| | | | |
|---|---|---|---|
| 4,210,172 A | 7/1980 | Clements et al. | |
| 4,241,757 A | 12/1980 | Bron | |
| 4,299,220 A | 11/1981 | Dorman | |
| 4,447,224 A | 5/1984 | DeCant, Jr. et al. | |
| 4,594,058 A | 6/1986 | Fischell | |
| 4,925,451 A | 5/1990 | Amendolia | |
| 5,067,943 A | 11/1991 | Burke | |
| 5,088,983 A | 2/1992 | Burke | |
| 5,242,406 A | 9/1993 | Gross et al. | |
| 6,203,523 B1 | 3/2001 | Haller et al. | |
| 6,589,205 B1 | 7/2003 | Meadows | |

FOREIGN PATENT DOCUMENTS

| | | |
|---|---|---|
| EP | 0 409 511 A1 | 1/1991 |
| EP | 0 420 620 A2 | 4/1991 |
| FR | 562137 A | 11/1923 |
| WO | WO 03/099351 | 12/2003 |

*Primary Examiner*—Nicholas D Lucchesi
*Assistant Examiner*—Laura A Bouchelle
(74) *Attorney, Agent, or Firm*—Scott A. Marks

(57) ABSTRACT

A drug delivery system (10) has a positive pressure drug reservoir (15). A pump (19) is in fluid communication with the reservoir (15) via a first fluid passageway (18). The outlet (19b) of the pump (19) is in fluid communication with a first regulator (21). The regulator (21) includes a housing (24) that has a first subchamber (24a) and a second subchamber (24b). The second subchamber (24b) is divided into a lower chamber (28a) and a middle chamber (28b) by a diaphragm (28). A third fluid passageway (32) is positioned between the lower chamber (28a) and the drug reservoir (15), whereby accidental flow from the reservoir (15) to an outlet (21b) is prevented.

19 Claims, 1 Drawing Sheet

DRUG DELIVERY SYSTEM

FIELD OF THE INVENTION

This invention relates generally to an implantable drug delivery system for delivering a liquid drug.

BACKGROUND OF THE INVENTION

There are several commercially available implantable medication delivery devices. Two such devices are provided by Medtronic, Inc. of Minneapolis, Minn. These include the Synchromed product as well as the MIP product. A propellant is utilized to maintain a constant absolute pressure at body temperature. The reservoir and the inlet side of the pump mechanism are at a constant absolute pressure while the tip of the output catheter and thus the outlet of the pump mechanism are at an ambient pressure. The ambient pressure may vary depending upon environmental conditions such as local barometric pressure and altitude, etc. Variations in temperature of the body in which the device is implanted may also affect the device. Because of the critical nature of such drug delivery systems, it always a desire to provide for a system with additional features.

BRIEF SUMMARY OF THE INVENTION

In a first embodiment, the invention is a drug delivery system for implantation in a body for delivery of a liquid drug, the system includes an infusion housing defining a drug reservoir. A propellant chamber is within the infusion housing and proximate the drug reservoir, wherein a positive pressure drug reservoir is created. The drug reservoir has a reservoir inlet for receiving the liquid drug and a reservoir outlet. A pump has a pump inlet and a pump outlet. A first fluid passageway is operable to transfer the liquid drug between the reservoir outlet and the pump inlet. A first regulator has a first subchamber having a first regulator outlet and a second subchamber having a first regulator inlet. A first opening is between the first subchamber and the second subchamber. A first diaphragm is positioned in the second subchamber, the diaphragm moveable between an open position and a closed position to open and close the first opening, the diaphragm separating the second subchamber into a first middle chamber and a first lower chamber. A second fluid passageway is operable to transfer the liquid drug between the pump outlet and the first regulator inlet, the regulator inlet positioned in the first middle chamber. A third fluid passageway is provided between the lower chamber and the drug reservoir, whereby accidental flow from the reservoir to the first outlet is prevented.

In another embodiment, the invention is a drug delivery system for implantation in a body for delivery of a liquid drug. The system includes an infusion housing defining a drug reservoir. A propellant chamber is within the infusion housing and proximate the drug reservoir, wherein a positive pressure drug reservoir is created. A drug reservoir has a fluid inlet for receiving the liquid drug and a reservoir outlet. A pump has a pump inlet and a pump outlet. A first passageway is operable to transfer the liquid drug between the reservoir outlet and the pump inlet. A first regulator has a first subchamber having a first regulator outlet and a second subchamber having a first regulator inlet. A first opening is positioned between the first subchamber and the second subchamber. A first diaphragm is positioned in the second subchamber. The first diaphragm is moveable between an open position and a closed position to open and close the first opening. The diaphragm separates the second subchamber into a first middle chamber and a first lower chamber. The second fluid passageway is operable to transfer the liquid drug between the pump outlet and the first regulator inlet. The first regulator inlet is positioned in the first middle chamber. The second regulator has a third subchamber having a second regulator outlet and a fourth subchamber having a second regulator inlet. A second opening is between the third subchamber and the fourth subchamber. A second diaphragm is positioned in the fourth subchamber. The second diaphragm is moveable between an open position and a closed position to open and close the second opening. The second diaphragm separates the fourth subchamber into a second middle chamber and a second lower chamber. A third passageway is positioned between the first regulator outlet and the second regulator inlet. A fourth fluid passageway is between the first lowered chamber and the drug reservoir, whereby accidental flow from the reservoir to the second outlet is prevented.

In another embodiment, the invention is a drug delivery system for implantation in a body for delivery of a liquid drug. This system includes an infusion housing defining a drug reservoir. A propellant chamber is within the infusion housing and proximate the drug reservoir, wherein a positive pressure drug reservoir is created. The drug reservoir has a reservoir inlet for receiving the liquid drug and a reservoir outlet. A pump has a pump inlet and a pump outlet. A first fluid passageway is operable to transfer the liquid drug between the reservoir outlet and the pump inlet. A first regulator has a first dividing member, the dividing member forming a first subchamber and a second subchamber. The first dividing member defining a first opening centrally located in the first dividing member. The first diaphragm is positioned in the second subchamber. The first diaphragm is moveable between an open position and a closed position to open and close the first opening. The diaphragm separates the second subchamber into a first middle chamber and a first lower chamber. A second fluid passageway operably transfers the liquid drug between the pump outlet and the first regulator inlet. The first regulator inlet position in the first middle chamber. A second regulator has a second dividing member. The second dividing member forms a third subchamber and a fourth subchamber. The second dividing member defines a second opening centrally located in the second dividing member. A second diaphragm is positioned in the fourth subchamber. The second diaphragm moveable between an open position and a closed position to open and close the second opening. The second diaphragm separating the fourth subchamber into a second middle chamber and a second lower chamber. A third fluid passageway is between the first regulator outlet and the second regulator inlet. A fourth fluid passageway is between the first lower chamber and the drug reservoir, whereby accidental flow from the reservoir to the outlet is prevented.

DETAILED DESCRIPTION OF THE INVENTION

Figure 1:
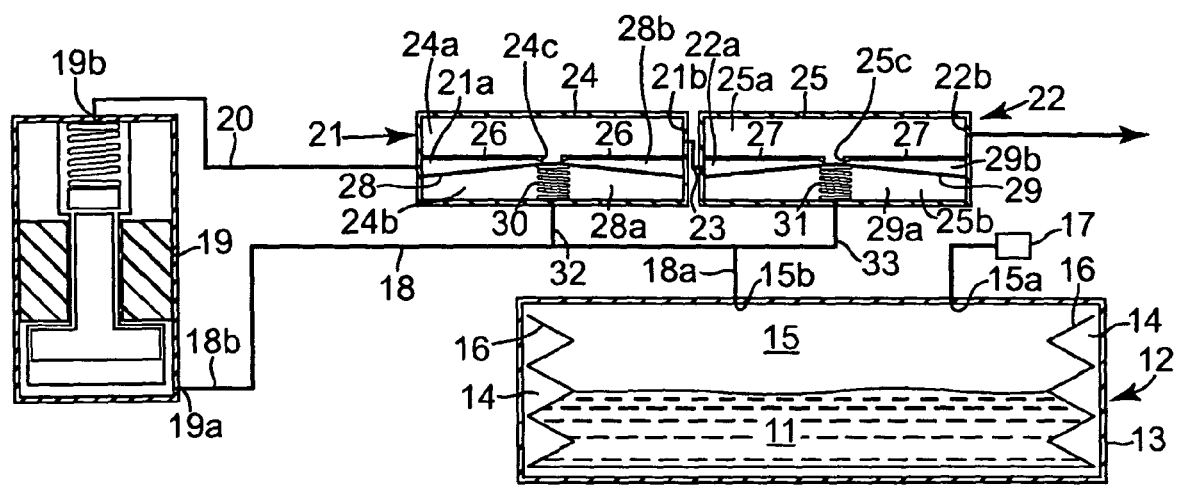
FIG. 1 shows an embodiment of a drug delivery system in accordance with the present invention.

Referring to the figures, wherein like numerals represent like parts throughout the several views, there is generally disclosed at 10 a drug delivery system. The drug delivery system 10 is for implanting in a body for delivery of a liquid drug. The drug delivery system 10 includes a drug reservoir 12 that includes a housing 13 that is divided into two chambers. The first chamber 14 is a propellant chamber and the second chamber 15 is the drug reservoir chamber. A metal bellows 16 divides the housing 13 into the two chambers 14, 15. A refill septum 17 is in fluid communication with an inlet 15a of a drug reservoir chamber 15 to allow for subcutaneous refilling of the drug reservoir chamber 15 with a drug 11. The drug reservoir chamber 15 has an outlet 15b that is in fluid communication with a first end 18a of fluid passageway 18. A second end 18b of the fluid passageway 18 is in fluid communication with an inlet 19a of pump 19. The pump 19 has an outlet 19b. The pump 19 may be any suitable pump such as a pump having a reciprocal piston or diaphragm. The outlet 19b of pump 19 is in fluid communication via a fluid passageway 20 to regulators 21, 22.

The regulators 21, 22 are connected in series via a fluid passageway 23. However, it is understood that only one regulator may be utilized for the present invention. The regulators 21, 22 are similar. The regulators 21, 22 include a housing 24, 25. A dividing member 26, 27 separates the chamber inside of the housing 24, 25 into two subchambers, a first subchamber 24a, 25a and a second subchamber 24b, 25b. The dividing member 26, 27 has a central aperture 24c, 25c. The central aperture 24c, 25c is approximately 0.010 inches in diameter, although other suitable sizes may also be utilized. The central aperture 24c, 25c, in cross-section, is less than one percent of the cross-sectional area of the dividing member 26, 27. A flexible diaphragm 28, 29 separates the second subchamber 24b, 25b into lower subchambers 28a, 29a and middle subchambers 28b, 29b, although it is understood that "lower" is being utilized only with respect to the orientation shown in FIG. 1. The diaphragms 28, 29 may be constructed from any suitable material such as titanium or silicone. It is understood that other orientations could also be used, i.e., the lower chamber 28a, 29a could be upper if rotated 180 degrees. The regulator 21, 22 has an inlet 21a, 22a that is positioned between the dividing member 26, 27 and the flexible diaphragm 28, 29. The regulator 21, 22 has an outlet 21b, 22b in the first subchamber 24a, 25a. The fluid passageway 20 places the outlet 19b of the pump 19 in fluid communication with the inlet 21a of the regulator 21. Fluid passageway 23 places the outlet 21b in fluid communication with the inlet 22a. The outlet 22b is adapted and configured to receive a suitable outside device such as a catheter. A spring 30, 31 is positioned between the flexible diaphragm 28, 29 and the housing 24, 25 to provide a biasing force that urges the diaphragm 28, 29 upward to close the central aperture 24c, 25c. The fluid passageway 18 is placed in fluid communication with the lower chamber 28a, 29a by fluid passageway 32, 33. Therefore, the lower subchamber 28a, 29a is at the same pressure as the drug reservoir chamber 15.

Figure 2:
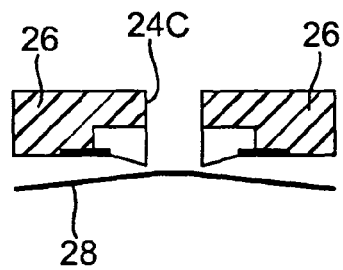
FIG. 2 shows an enlargement of a portion of one of the regulators shown in FIG. 1.

In operation, the drug 11 is delivered to the drug reservoir chamber 15 through the refill septum 17. When the pump 19 is activated, the drug 11 is drawn out of the reservoir 15 and delivered to the pump 19 via fluid passageway 18. The drug 11 exits the pump through fluid passageway 20 and enters the first regulator 21 between the dividing member 26 and the flexible diaphragm 28. This creates a larger pressure in the middle subchamber 28b than in the lower subchamber 28a, causing the diaphragm 28 to move downward and open the passageway through the central aperture 24c, as shown in FIG. 2. The drug 11 then passes into the first subchamber 24a and exits through the fluid passageway 23 into the middle subchamber 29b. Again, since the pressure is greater in middle subchamber 29b than in the lower subchamber 29a, the flexible diaphragm 29 is moved away from the central aperture 25c and the drug 11 moves into the first subchamber 25a and out the outlet 22b. The present regulator is designed so that the drug being delivered from the pump 19 acts against a large portion of the flexible diaphragm 28, 29 so that the most force will be generated for a given pressure. The drug will be acting against over 95 percent of the diaphragm, and preferably over 99 percent of the diaphragm to generate the force against the flexible diaphragm 28, 29. The valve formed by the flexible diaphragm 28, 29 and the central aperture 24c, 25c will therefore tend to be stable and shut off quickly as opposed to the prior art devices which would tend to have hysteresis and close slower. With the present invention, as the drug leaks out of the outlet 22b, the diaphragm 28, 29 will tend to hover between the open and closed position and not jump back as much as in the prior art devices. The present invention will tend to open and close more smoothly and therefore be more predictable.

If, for example, the drug reservoir chamber 15 is at 5 psig, the pump 19 having a check valve on its outlet in the 2-5 psi range, 2 psi will be required to open the valves in the regulators 21, 22. The spring may have any suitable force, such as from 10 to 100 grams. High pressure is thereby maintained through both regulators 21, 22 so that bubbles will not form in the pump 19. Since low pressure may tend to pull gasses out of a solution, the pressure is maintained from the reservoir through the pump to the valve. It is preferred to have the pressure drop through the valve and not the pump.

Thus, embodiments of the Drug Delivery System are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A drug delivery system for implantation in a body for delivery of a liquid drug, the system comprising:
    a) an infusion housing defining a drug reservoir, a propellant chamber within the infusion housing and proximate the drug reservoir, wherein a positive pressure drug reservoir is created;
    b) the drug reservoir having a reservoir inlet for receiving the liquid drug and a reservoir outlet;
    c) a pump having a pump inlet and a pump outlet;
    d) a first fluid passageway operable to transfer the liquid drug between the reservoir outlet and the pump inlet;
    e) a first regulator having a first subchamber having a first regulator outlet and a second subchamber having a first regulator inlet;
    f) a first opening between the first subchamber and the second subchamber;
    g) a first diaphragm positioned in the second subchamber, the diaphragm moveable between an open position and a closed position to open and close the first opening, the diaphragm separating the second subchamber into a first middle chamber and a first lower chamber;
    h) a second fluid passageway operable to transfer the liquid drug between the pump outlet and the first regulator inlet, the first regulator inlet positioned in the first middle chamber; and
    i) a third fluid passageway between the lower chamber and the drug reservoir, whereby accidental flow from the reservoir to the first regulator outlet is prevented.

2. The drug delivery system of claim 1, further comprising a dividing member, the dividing member forming the first subchamber and the second subchamber.

3. The drug delivery system of claim 2, wherein the first opening is defined by the dividing member and the first opening is centrally located in the dividing member.

4. The drug delivery system of claim 3, wherein the diaphragm is closed when the pump is not activated, thereby maintaining a high pressure in the regulator to prevent formation of bubbles.

5. The drug delivery system of claim 3, wherein the opening is less than 0.020 inches in diameter.

6. The drug delivery system of claim 3, wherein pressure from delivery of the drug to the first regulator acts on at least 95 percent of the diaphragm, whereby hysteresis of the diaphragm is reduced.

7. The drug delivery system of claim 1, further comprising a second regulator, the second regulator comprising:
  a) third subchamber having a second regulator outlet and a fourth subchamber having a second regulator inlet;
  b) a second opening between the third subchamber and the fourth subchamber;
  c) a second diaphragm positioned in the fourth subchamber, the second diaphragm moveable between an open position and a closed position to open and close the second opening, the second diaphragm separating the fourth subchamber into a second middle chamber and a second lower chamber; and
  d) a fourth fluid passageway between the first regulator outlet and the second regulator inlet.

8. A drug delivery system for implantation in a body for delivery of a liquid drug, the system comprising:
  a) an infusion housing defining a drug reservoir, a propellant chamber within the infusion housing and proximate the drug reservoir, wherein a positive pressure drug reservoir is created;
  b) the drug reservoir having a reservoir inlet for receiving the liquid drug and a reservoir outlet;
  c) a pump having a pump inlet and a pump outlet;
  d) a first fluid passageway operable to transfer the liquid drug between the reservoir outlet and the pump inlet;
  e) a first regulator having a first subchamber having a first regulator outlet and a second subchamber having a first regulator inlet;
  f) a first opening between the first subchamber and the second subchamber;
  g) a first diaphragm positioned in the second subchamber, the first diaphragm moveable between an open position and a closed position to open and close the first opening, the diaphragm separating the second subchamber into a first middle chamber and a first lower chamber;
  h) a second fluid passageway operable to transfer the liquid drug between the pump outlet and the first regulator inlet, the first regulator inlet positioned in the first middle chamber;
  i) a second regulator having a third subchamber having a second regulator outlet and a fourth subchamber having a second regulator inlet;
  j) a second opening between the third subchamber and the fourth subchamber;
  k) a second diaphragm positioned in the fourth subchamber, the second diaphragm moveable between an open position and a closed position to open and close the second opening, the second diaphragm separating the fourth subchamber into a second middle chamber and a second lower chamber;
  l) a third fluid passageway between the first regulator outlet and the second regulator inlet; and
  m) a fourth fluid passageway between the first lower chamber and the drug reservoir, whereby accidental flow from the reservoir to the second regulator outlet is prevented.

9. The drug delivery system of claim 8, further comprising a fifth fluid passageway between the second lower chamber and the drug reservoir.

10. The drug delivery system of claim 9, wherein the first and second openings are centrally located.

11. The drug delivery system of claim 10, wherein the diaphragm is closed when the pump is not activated, thereby maintaining a high pressure in the regulator to prevent formation of bubbles.

12. The drug delivery system of claim 11, wherein the openings are less than 0.020 inches in diameter.

13. The drug delivery system of claim 12, wherein pressure from delivery of the drug to the first regulator acts on at least 95 percent of the diaphragms, whereby hysteresis of the diaphragm is reduced.

14. A drug delivery system for implantation in a body for delivery of a liquid drug, the system comprising:
  a) an infusion housing defining a drug reservoir, a propellant chamber within the infusion housing and proximate the drug reservoir, wherein a positive pressure drug reservoir is created;
  b) the drug reservoir having a reservoir inlet for receiving the liquid drug and a reservoir outlet;
  c) a pump having a pump inlet and a pump outlet;
  d) a first fluid passageway operable to transfer the liquid drug between the reservoir outlet and the pump inlet;
  e) a first regulator having a first dividing member, the first dividing member forming a first subchamber and a second subchamber, the first dividing member defining a first opening centrally located in the first dividing member;
  f) a first diaphragm positioned in the second subchamber, the first diaphragm moveable between an open position and a closed position to open and close the first opening, the first diaphragm separating the second subchamber into a first middle chamber and a first lower chamber;
  g) a second fluid passageway operable to transfer the liquid drug between the pump outlet and the first regulator inlet, the first regulator inlet positioned in the first middle chamber;
  h) a second regulator having a second dividing member, the second dividing member forming a third subchamber and a fourth subchamber, the second dividing member defining a second opening centrally located in the second dividing member;
  i) a second diaphragm positioned in the fourth subchamber, the second diaphragm moveable between an open position and a closed position to open and close the second opening, the second diaphragm separating the fourth subchamber into a second middle chamber and a second lower chamber; and
  j) a third fluid passageway between the first regulator outlet and the second regulator inlet; and
  k) a fourth fluid passageway between the first lower chamber and the drug reservoir, whereby accidental flow from the reservoir to the second regulator outlet is prevented.

15. The drug delivery system of claim 14, further comprising a fifth fluid passageway between the second lower chamber and the drug reservoir.

16. The drug delivery system of claim 15, wherein the first and second openings are centrally located.

17. The drug delivery system of claim 16, wherein the diaphragm is closed when the pump is not activated, thereby maintaining a high pressure in the regulator to prevent formation of bubbles.

18. The drug delivery system of claim 17, wherein the openings are less than 0.020 inches in diameter.

19. The drug delivery system of claim 18, wherein pressure from delivery of the drug to the first regulator acts on at least 95 percent of the diaphragms, whereby hysteresis of the diaphragm is reduced.

* * * * *